United States Patent
Kafri

(10) Patent No.: US 10,017,785 B2
(45) Date of Patent: Jul. 10, 2018

(54) POLYPURINE TRACT MODIFIED RETROVIRAL VECTORS

(71) Applicant: The University of North Carolina at Chapel Hill, Chapel Hill, NC (US)

(72) Inventor: Tal Kafri, Carrboro, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 15/790,530

(22) Filed: Oct. 23, 2017

(65) Prior Publication Data

US 2018/0119170 A1      May 3, 2018

Related U.S. Application Data

(63) Continuation of application No. 12/747,076, filed as application No. PCT/US2008/086409 on Dec. 11, 2008, now Pat. No. 9,796,987.

(60) Provisional application No. 61/007,118, filed on Dec. 11, 2007.

(51) Int. Cl.
| | |
|---|---|
| *C12P 19/34* | (2006.01) |
| *C12N 15/86* | (2006.01) |
| *C12N 15/63* | (2006.01) |
| *C12N 15/67* | (2006.01) |
| *C12N 5/10* | (2006.01) |
| *C12N 7/01* | (2006.01) |

(52) U.S. Cl.
CPC .... *C12N 15/86* (2013.01); *C12N 2740/15043* (2013.01); *C12N 2740/16043* (2013.01); *C12N 2800/108* (2013.01); *C12N 2800/24* (2013.01)

(58) Field of Classification Search
CPC ......... C12P 19/34; C12N 15/63; C12N 15/67; C12N 5/10; C12N 7/01
See application file for complete search history.

(56) References Cited

U.S. PATENT DOCUMENTS

| | | |
|---|---|---|
| 6,613,752 B2 | 9/2003 | Kay et al. |
| 7,220,578 B2 | 5/2007 | Kafri et al. |
| 2003/0003565 A1 | 1/2003 | Dubensky, Jr. et al. |
| 2004/0170962 A1 | 9/2004 | Kafri et al. |
| 2005/0053929 A1 | 3/2005 | Sharpe et al. |
| 2006/0019393 A1 | 1/2006 | Cannon et al. |
| 2006/0281128 A1 | 12/2006 | Lu et al. |

FOREIGN PATENT DOCUMENTS

| | | |
|---|---|---|
| EP | 1 757 703 A2 | 2/2007 |
| WO | WO 96/07741 A1 | 3/1996 |
| WO | WO 97/20060 A1 | 6/1997 |
| WO | WO 2004/022761 A1 | 3/2004 |
| WO | WO 2005/052171 A2 | 6/2005 |
| WO | WO 2009/076524 A2 | 6/2009 |

OTHER PUBLICATIONS

Araki et al. "Site-directed integration of the cre gene mediated by Cre recombinase using a combination of mutant lox sites" *Nucleic Acids Research* 30(19):e103 (2002).
Arkhipova et al. "Diverse DNA transposons in rotifers of the class Bdelloidea" *Proceedings of the National Academy of Sciences* 102(33):11781-11786 (2005).
Bayer et al. "A Large U3 Deletion Causes Increased In Vivo Expression From a Nonintegrating Lentiviral Vector" *Molecular Therapy* 16(12):1968-1976 (2008).
Decision to Grant corresponding to Japanese Patent Application No. 2010-538155 (dated Apr. 27, 2015).
Extended European Search Report corresponding to European Patent Application No. 08859393.4 (dated Nov. 29, 2011).
Hacein-Bey-Abina et al. "LMO2-Associated Clonal T Cell Proliferation in Two Patients after Gene Therapy for SCID-X1" *Science* 302:415-419 (2003).
Hirt, Bernard "Selective Extraction of Polyoma DNA from Infected Mouse Cell Cultures" *Journal of Molecular Biology* 26:365-369 (1967).
Hungnes et al. "Mutations in the Central Polypurine Tract of HIV-1 Result in Delayed Replication" *Virology* 190:440-442 (1992).
International Preliminary Report on Patentability corresponding to International Patent Application No. PCT/US2008/086409 (dated Jun. 24, 2010).
International Search Report and the Written Opinion of the International Searching Authority corresponding to International Patent Application No. PCT/US2008/086409 (dated Jul. 24, 2009).
Ivics et al. "Molecular Reconstruction of Sleeping Beauty, a Tc1-like Transposon from Fish, and Its Transposition in Human Cells" *Cell* 91:501-510 (1997).

(Continued)

*Primary Examiner* — Antonio Galisteo Gonzalez
(74) *Attorney, Agent, or Firm* — Myers Bigel, P.A.

(57) ABSTRACT

An integration-defective retroviral vector transfer cassette lacking a functional polypurine tract (PPT) is provided. Also provided are isolated nucleic acids that include a heterologous nucleotide sequence, one or two retroviral long terminal repeats (LTRs), a packaging signal, a rev responsive element, and a eukaryotic promoter, wherein the nucleic acid lacks a functional PPT; vectors that include the disclosed isolated nucleic acids; recombinant retroviral particles and mRNAs thereof; retroviral vector kits; and methods for producing integration-defective vector particles, achieving gene expression of a nucleotide sequence of interest, and inserting a nucleotide sequence of interest into a host cell genome in a site-specific or non-specific manner.

10 Claims, 7 Drawing Sheets

(56) References Cited

OTHER PUBLICATIONS

Johnson et al. "Replication of Flock House Virus RNAs from Primary Transcripts Made in Cells by RNA Polymerase II" *Journal of Virology* 71(4):3323-3327 (1997).
Kantor et al. "Notable Reduction in Illegitimate Integration Mediated by a PPT-deleted, Nonintegrating Lentiviral Vector" *Molecular Therapy* 19(3):547-556 (2011).
Kuroda et al. "Flip-Flop HSV-BAC: bacterial artificial chromosome based system for rapid generation of recombinant herpes simplex virus vectors using two independent site-specific recombinases" *BMC Biotechnology* 6(40):1-19 (2006).
Li et al. "Murine Leukemia Induced by Retroviral Gene Marking" *Science* 296:497 (2002).
Ma et al. "A Single-LTR HIV-1 Vector Optimized for Functional Genomics Applications" *Molecular Therapy* 10(1):139-149 (2004).
Miles et al. "Effect of Polypurine Tract (PPT) Mutations on Human Immunodeficiency Virus Type 1 Replication: a Virus with a Completely Randomized PPT Retains Low Infectivity" *Journal of Virology* 79(11):6859-6867 (2005).
Nightingale et al. "Transient Gene Expression by Nonintegrating Lentiviral Vectors" *Molecular Therapy* 13(6):1121-1132 (2006).
Office Action corresponding to European Patent Application No. 08859393.4 (dated Apr. 15, 2014).
Office Action corresponding to Japanese Patent Application No. 2010-538155 (dated Nov. 5, 2013).
Philippe et al. "Lentiviral vectors with a defective integrase allow efficient and sustained transgene expression in vitro and in vivo" *Proceedings of the National Academy of Sciences* 103(47):17684-17689 (2006).
Philpott et al. "Use of Nonintegrating Lentiviral Vectors for Gene Therapy" *Human Gene Therapy* 18:1-7 (2007).
Plasterk et al. "Resident aliens: the Tc1/mariner superfamily of transposable elements" *Trends in Genetics* 15(8):326-332 (1999).
Rausch et al. "'Binding, bending and bonding': polypurine tract-primed initiation of plus-strand DNA synthesis in human immunodeficiency virus" *The International Journal of Biochemistry & Cell Biology* 36:1752-1766 (2004).
Robertson, Hugh M. "The mariner transposable element is widespread in insects" *Nature* 362:241-245 (1993).
Robson et al. "Effects of 3' Untranslated Region Mutations on Plus-Strand Priming during Moloney Murine Leukemia Virus Replication" *Journal of Virology* 73(2):948-957 (1999).
Sau et al. "Biochemical and Kinetic Analysis of the RNase Active Sites of the Integrase/Tyrosine Family Site-specific DNA Recombinases" *The Journal of Biological Chemistry* 276(49):46612-46623 (2001).
Vargas et al. "Novel Integrase-Defective Lentiviral Episomal Vectors for Gene Transfer" *Human Gene Therapy* 15:361-372 (2004).
Vieira et al. "The pUC plasmids, an M13mp7-derived system for insertion mutagenesis and sequencing with synthetic universal primers" *Gene* 19(3):259-268 (1982) (Abstract only).
Wu, Yuntao "HIV-I gene expression: lessons from provirus and non-integrated DNA" *Retrovirology* 1(13):1-10 (2004).
Yañez-Muñoz et al. "Effective gene therapy with nonintegrating lentiviral vectors" *Nature Medicine* 12(3):348-353 (2006).
Zayed et al. "The DNA-bending protein HMGB1 is a cellular cofactor of Sleeping Beauty transposition" *Nucleic Acids Research* 31(9):2313-2322 (2003).
Zufferey et al. "Woodchuck Hepatitis Virus Posttranscriptional Regulatory Element Enhances Expression of Transgenes Delivered by Retroviral Vectors" *Journal of Virology* 73(4):2886-2892 (1999).
Extended European Search Report corresponding to European Patent Application No. 17204678.1 (10 pages) (dated Mar. 20, 2018).

POLYPURINE TRACT MODIFIED RETROVIRAL VECTORS

CROSS REFERENCE TO RELATED APPLICATIONS

This application is a continuation application of, and claims priority to, U.S. patent application Ser. No. 12/747,076, filed Aug. 27, 2010, and issued as U.S. Pat. No. 9,796,087 on Oct. 24, 2017, which claims the benefit of PCT International Application No. PCT/US08/86409, filed Dec. 11, 2008, which claims priority to U.S. Provisional Patent Application Ser. No. 61/007,118 filed Dec. 11, 2007, the disclosure of each of which is incorporated herein by reference in its entirety.

STATEMENT OF GOVERNMENT INTEREST

This invention was made with government support under Grant No. 2R56DK058702-06A1 awarded by the National Institutes of Health. The government has certain rights in the invention.

TECHNICAL FIELD

The presently disclosed subject matter pertains to integration-defective retroviral vectors and methods for using the same, such as in gene therapy and in basic biology research.

BACKGROUND

The capacity to introduce a particular foreign or native gene sequence into a cell and to control the expression of that gene is of value in the fields of medicine and biological research. Such capacity has a wide variety of useful applications, including but not limited to studying gene regulation and designing a therapeutic basis for the treatment of disease.

The introduction of a particular foreign or native gene into a host cell can be facilitated by introducing a gene sequence into a suitable nucleic acid vector. A variety of methods have been developed that allow the introduction of such a recombinant vector into a desired host cell. The use of viral vectors can result in the rapid introduction of the recombinant molecule into a wide variety of host cells.

Retroviruses are RNA viruses that replicate through a DNA proviral intermediate that is usually integrated in the genome of the infected host cell. All known retroviruses share features of the replicative cycle, including packaging of viral RNA into virions, entry into target cells, reverse transcription of viral RNA to form the DNA provirus, and stable integration of the provirus into the target cell genome. Replication competent simple proviruses typically comprise regulatory long terminal repeats (LTRs) and the gag, pro, pol and env genes which encode core proteins (gag), a protease (pro), reverse transcriptase (pol), RNAse H (pol), integrase (pol) and envelope glycoproteins (env). Complex retroviruses also typically comprise additional accessory genes.

Retroviral vectors are a common tool for gene delivery in that the ability of retroviral vectors to deliver an unrearranged, single copy gene into a broad range of cells makes them well suited for transferring genes to a cell. While recombinant retroviral vectors allow for integration of a transgene into a host cell genome, most retroviruses can only transduce dividing cells. This can limit their use for in vivo gene transfer to non-proliferating cells such as hepatocytes, myofibers, hematopoietic stein cells (HSCs), and neurons. Non-dividing cells are the predominant, long-lived cell type in the body, and account for most desirable targets of gene transfer, including liver, muscle, and brain.

Lentiviruses are a subgroup of retroviruses that are capable of infecting non-dividing cells. These viruses include, but are not limited to, HIV-1, HIV-2, SIV, EIAV, and FIV. Lentiviruses possess gag, pol, and env genes in addition to other accessory genes that are flanked by two long terminal repeat (LTR) sequences.

A key challenge for gene transfer based on the use of retroviral vectors is to achieve stable transgene expression while minimizing insertional mutagenesis and induction of the DNA damage response due to the presence of double stranded DNA. One approach to avoid insertional mutagenesis is to target the transgene integration to a specific location on the genome.

One approach to achieving transgene expression while minimizing insertional mutagenesis is to produce non-integrating lentiviral (NIL) vectors. NIL vectors have been produced by introducing combinations of mutations made to disable the integrase protein itself or to alter the integrase recognition sequences (att) in the viral LTR (see e.g., Yanez-Munoz et al. (2006) *Nat Med* 12(3):348-353; Nightingale et al. (2006) *Mol Ther* 13(6):1121-1132). Recent in vitro and in vivo studies show that NIL vectors can mediate stable transduction and allow for high levels of transgene expression (see e.g., Yanez-Munoz et al. (2006) *Nat Med* 12(3):348-353; Nightingale et al. (2006) *Mol Ther* 13(6):1121-1132). Therefore, the high efficiency of gene transfer and expression mediated by lentiviruses can be harnessed in vivo without a requirement for vector integration. However, the vector forms generated by the above approaches comprise linear as well as three types of circular episomal vector forms. The linear DNA forms, which constitute the majority of the episomal forms, carry the potential of inducing DNA damage response due to the presence of free double stranded DNA ends.

The presently disclosed subject matter provides improved integration-defective vector systems whose end product is a homogenous population of circular vector forms containing 1-LTR that are capable of mediating gene transfer into animal cells with a decreased risk of inducing DNA damage response. The fact that only 1-LTR forms are generated allows for better control of the non-integrating vectors. In addition, the new integration-defective vector system is significantly more efficient than the currently used non-integrating retroviral system in the context of particular applications, which are based on circular vector forms including but not limited to FLIP and cre mediated vector integration.

SUMMARY OF THE INVENTION

This Summary lists several embodiments of the presently disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently disclosed subject matter, whether listed in this Summary or not. To avoid excessive repetition, this Summary does not list or suggest all possible combinations of such features.

The presently disclosed subject matter provides integration-defective retroviral vector transfer cassettes lacking a functional polypurine tract (PPT). In some embodiments, the retroviral vector transfer cassettes lack a functional central polypurine tract (cPPT). In some embodiments, the retroviral vector transfer cassettes comprise a heterologous sequence.

The presently disclosed subject matter also provides isolated nucleic acids comprising a heterologous nucleotide sequence, one or two retroviral long terminal repeats (LTRs), a packaging signal, a rev responsive element, and a eukaryotic promoter, wherein the nucleic acid lacks a functional PPT. In some embodiments, the nucleic acids comprise a viral origin of replication or a sequence that can directly or indirectly mediate replication of the vector nucleic acid by a host. In some embodiments, the nucleic acids comprise a bacterial origin of replication and a bacterial selection marker situated between the two LTRs. In some embodiments, the viral origin of replication is selected from the group consisting of Epstein-Barr Virus OriP and an SV40 origin of replication. In some embodiments, the sequence that can directly or indirectly mediate replication of the vector nucleic acid by the host cell is selected from the group consisting of (a) a sequence recognized by the host-cell replication machinery; (b) a sequence encoding a protein that can associate with and/or modulate host-cell replication machinery; and (c) a sequence encoding a protein that can associate with the protein of part (b) or can recognize a sequence of the vector. In some embodiments, the heterologous sequence is selected from the group consisting of one or more marker genes, therapeutic genes, antiviral genes, antitumor genes, cytokine genes, genes encoding antigens, sequences that can associate with the host chromatin, sequences that encode a protein that can associate with the host DNA and the host chromatin and the nucleic acid of the vector, sequences that encode a protein having DNA methylation activity, DNA de-methylation activity, and/or cytidine deamination activity, and combinations thereof. In some embodiments, the heterologous sequence is a nucleotide sequence from a genes associated with dedifferentiation and/or the establishment of induced pluripotent stem cells (iPS) such as, but not limited to Oct4, Nanog, Klf4, Sox2, FGF-4, Ssea-1, Stat-3, and Myc. In some embodiments, the marker genes are selected from the group consisting of β-galactosidase gene, hygromycin gene, blasticidin gene, MGMT gene, neomycin gene, puromycin gene, cytosine deaminase gene, secreted alkaline phosphatase gene, fluorescent protein genes, and combinations thereof. In some embodiments, the nucleic acids lack a functional cPPT. In some embodiments, the nucleic acids comprise a post-transcriptional regulatory element (PRE). In some embodiments, a PRE comprises a Woodchuck hepatitis virus post-transcriptional regulatory element.

In some embodiments, the presently disclosed nucleic acids are present in a vector. In some embodiments, the vector comprises only a single LTR. In some embodiments, the vector comprises a self inactivating deletion in the U3 region of the LTR. In some embodiments, the deleted portion of the U3 region is replaced with an inducible promoter. In some embodiments, the presently disclosed vectors comprise a site-directed recombination site. In some embodiments, the site-directed recombination site is in the U3 region of the LTR. In some embodiments, the site-directed recombination site is selected from the group consisting of loxP and FRT. In some embodiments, the presently disclosed vectors comprise a restriction site in the U3 region of the LTR. In some embodiments, the vector comprises sequences from at least two different retroviruses. In some embodiments, the at least two different retroviruses includes a lentivirus. In some embodiments, the vector LTR comprises sequences from at least two different retroviruses. In some embodiments, the at least two different retroviruses includes a lentivirus. In some embodiments, the vector comprises sequences from at least two different retroviruses and at least one of the sequences encodes a cis element that provides for cross-packaging of the vector in a viral particle. In some embodiments, the cis element is selected from the group consisting of a RRE, an Env gene fragment from the region flanking the RRE, and a cPPT.

The presently disclosed subject matter also provides recombinant retroviral particles comprising the presently disclosed vectors. In some embodiments, the recombinant retroviral particle is intended for use in gene therapy.

The presently disclosed subject matter also provides retroviral proviruses produced by infection of target cells with the presently disclosed recombinant retroviral particles.

The presently disclosed subject matter also provides mRNA or another RNA of the presently disclosed retroviral proviruses.

The presently disclosed subject matter also provides inducible retroviral vector packaging cell lines comprising the presently disclosed retroviral vectors claim 3 or 13 and at least one construct encoding one or more proteins required for the retroviral vector to be packaged.

The presently disclosed subject matter also provides retroviral vector kits. In some embodiments, the retroviral kits comprise (a) an integration-defective retroviral vector transfer cassette lacking a functional PPT; and (b) a packaging cell line comprising at least one construct encoding one or more proteins required for the retroviral vector to be packaged.

The presently disclosed subject matter also provides methods for producing integration-defective vector particles. In some embodiments, the methods comprise transfecting a packaging cell line with an integration-defective retroviral vector transfer cassette lacking a functional PPT, wherein the packaging cell line provides proteins for the retroviral vector to be packaged.

The presently disclosed subject matter also provides methods for expressing a nucleotide sequence of interest in a cell of an animal without integration of the nucleotide sequence into the animal's genome. In some embodiments, the methods comprise infecting one or more cells with the presently disclosed integration-defective retroviral particles.

The presently disclosed subject matter also provides methods for inserting a nucleotide sequence of interest into a host cell genome in a site-specific manner. In some embodiments, the methods comprise (a) transducing a compatible host cell with a presently disclosed integration-defective vector comprising in operable combination the nucleotide sequence of interest and one or more site-directed recombination sequences; and (b) transfecting or transducing the compatible host cell with a nucleic acid comprising a sequence encoding a nuclease or recombinase that can mediate site-specific integration at the recombination sequence, wherein the transfecting or transducing of part (b) can occur separately or in the same step as part (a), wherein the nucleotide sequence of interest is inserted in a site-specific manner into the host cell genome. In some embodiments, the recombinase capable of mediating site-specific integration at the recombination sequence is Cre or FLP. In some embodiments, the transfecting or transducing of part (b) occurs in the same step as part (a) and the nucleic acid comprising a sequence encoding a nuclease or recombinase is the integration-defective vector of part (a). In some embodiments, the transfecting or transducing of part (b) occurs in the same step as part (a) and the nucleic acid comprising a sequence encoding a nuclease or recombinase is a separate vector, plasmid, or nucleic acid molecule than the integration-defective vector of part (a).

The presently disclosed subject matter also provides methods for inserting a nucleotide sequence of interest into a host cell genome in a non-specific manner. In some embodiments, the methods comprise (a) transducing a host cell with the integration-defective vector of claim 3 or 13, comprising in operable combination, the nucleotide sequence of interest and one or more transposon sequences; and (b) transfecting or transducing the host cell with a nucleic acid comprising a sequence encoding a transposase that can mediate integration into the host genome, wherein the transfecting or transducing of part (b) can occur separately or in the same step as part (a), wherein the nucleotide sequence of interest is inserted into the host cell genome. In some embodiments, the transfecting or transducing of part (b) occurs in the same step as part (a) and the nucleic acid comprising a sequence encoding a transposase is the integration-defective vector of part (a). In some embodiments, the transfecting or transducing of part (b) occurs in the same step as part (a) and the nucleic acid comprising a sequence encoding a transposase is a separate vector, plasmid or nucleic acid molecule than the integration-defective vector of part (a). In some embodiments, the transposon or transposase is of a mariner-type. In some embodiments, the transposon or transposase is Sleeping Beauty.

It is an object of the presently disclosed subject matter to provide integration-defective retroviral vector transfer cassettes that lack functional polypurine tracts.

An object of the presently disclosed subject matter having been stated hereinabove, and which is achieved in whole or in part by the presently disclosed subject matter, other objects will become evident as the description proceeds when taken in connection with the accompanying drawings as best described hereinbelow.

DETAILED DESCRIPTION

The ability of retroviral vectors to deliver large genetic payloads into non-dividing cells opens promising avenues for the introduction of one or more particular nucleic acid sequences into a cell. However, realizing the full potential of the retroviral vector system into a valid delivery modality is currently impeded by the potential for retroviral vector-induced insertional mutagenesis. Accordingly, the presently disclosed subject matter provides integration-deficient retroviral vectors, and methods of making and using the same, that address the risks associated with retroviral vector-mediated insertional mutagenesis, among other problems in the art.

Figure 1:
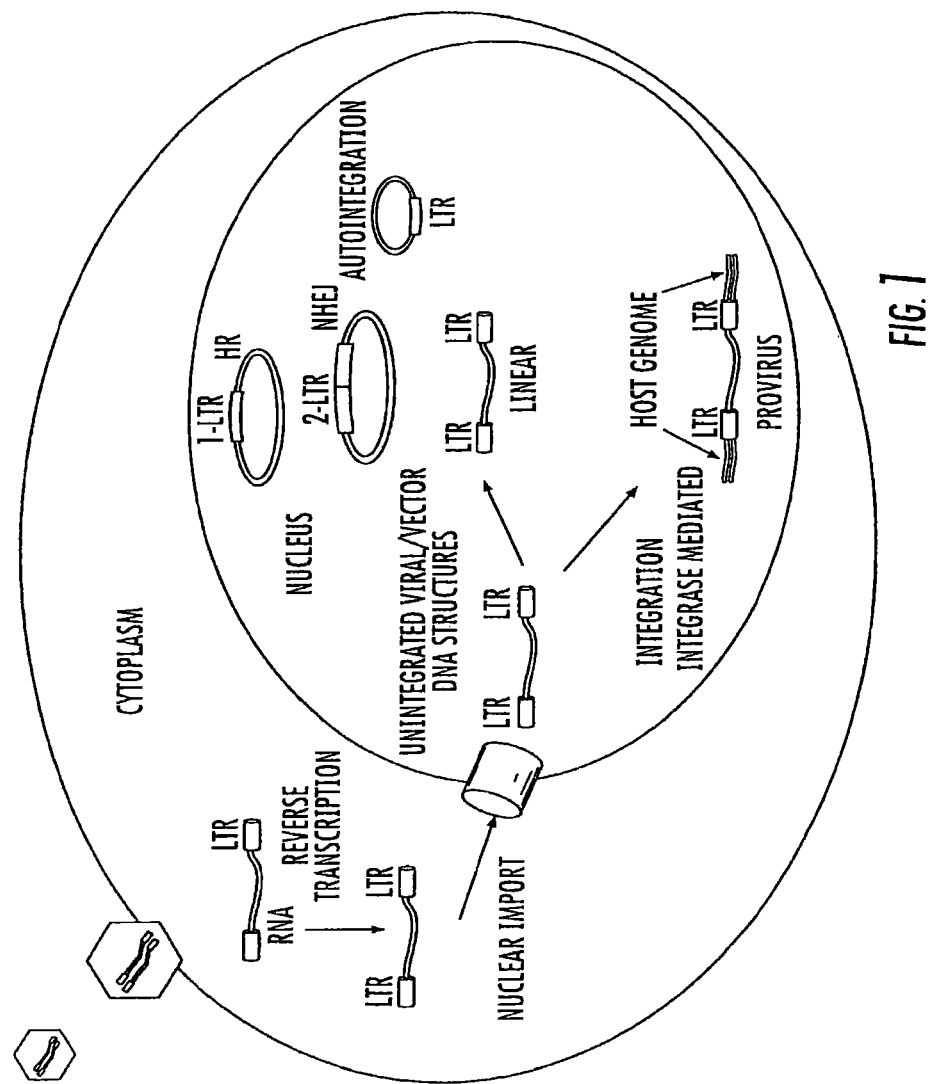
FIG. 1 is a schematic diagram depicting cellular factors affecting episome formation. Abbreviations: LTR—long terminal repeat; RNA—viral genomic RNA; 1-LTR—circular form with one LTR; 2-LTR—circular form with 2 LTRs; HR—host cell homologous recombination-based DNA repair pathway; NHEJ—host cell non-homologous DNA end joining (NHEJ) pathway.

Previous approaches for producing non-integrating retroviral vectors are premised on inhibiting the integration step of the vector life cycle during which the linear vector DNA is inserted into the host genome. In these previously described approaches, non-integrating retroviral vectors are generated by either employing integrase deficient packaging systems, or by mutating the vector's att sites. Consequently, the episomal vector forms generated by these approaches comprise either linear or various circular DNA forms including 1-LTR, 2-LTR, and autointegration-products (see FIG. 1).

In contrast, the approach provided in the presently disclosed subject matter is premised on generating non-integrating retroviral vectors by targeting the retroviral reverse transcription process, which precedes integration. The approach provided herein is premised on dramatically reducing the production of the vector linear DNA during reverse transcription and on generating essentially 1-LTR DNA circles only. The fact that essentially only 1-LTR forms are generated allows for better control of the non-integrating vectors. One benefit is that the dramatic reduction in vector linear DNA decreases the risk of induction of the DNA damage repair response. In addition, the new integration-defective vector system is significantly more efficient than the currently used non-integrating retroviral system in the context of particular applications, which are based on circular vector forms including but not limited to FLP and Cre mediated vector integration. Furthermore, the episomal 1-LTR forms of the presently disclosed subject matter that contain either a viral origin of replication or a sequence that can mediate replication of the vector nucleic acid by a host can be maintained in dividing target cells. Conversely, in applications where only transient gene expression is desired, the episomal 1-LTR forms of the presently disclosed subject matter that do not contain an origin of replication are useful as they are not maintained in dividing cells.

I. Definitions

It is to be understood that the terminology used herein is for the purpose of describing particular embodiments only and is not intended to be limiting. Unless defined otherwise, all technical and scientific terms used herein have the same meaning as commonly understood to one of ordinary skill in the art to which the presently disclosed subject matter belongs. Although any methods and materials similar or equivalent to those described herein can be used in the practice or testing of the presently disclosed subject matter, representative methods and materials are herein described. All publications, patent applications, patents, and other references mentioned herein are incorporated by reference in their entirety.

Following long-standing patent law convention, the terms "a", "an", and "the" refer to "one or more" when used in this application, including in the claims.

Unless otherwise indicated, all numbers expressing quantities of ingredients, reaction conditions, and so forth used in the specification and claims are to be understood as being modified in all instances by the term "about". Accordingly, unless indicated to the contrary, the numerical parameters set forth in the present specification and attached claims are approximations that can vary depending upon the desired properties sought to be obtained by the presently disclosed subject matter.

The term "about", as used herein when referring to a measurable value such as an amount of weight, time, dose, etc., is meant to encompass variations of in some embodiments ±20%, in some embodiments ±10%, in some embodiments ±5%, in some embodiments ±1%, and in some embodiments ±0.1% from the specified amount, as such variations are appropriate to perform the disclosed methods and/or employ the disclosed compositions.

As used herein, the term "cis-regulatory element" or "cis-element" has the same meaning as commonly understood to one of ordinary skill in the art; i.e., is a region of DNA or RNA which regulates the expression of genes located on that same strand of DNA or RNA.

As used herein, the term "compatible host cell" means a host cell having one or more site-directed recombination sequences in its genome that are compatible with the recombination sequences on an integration-defective vector of the presently disclosed subject matter. The compatible host cell recombination sequences are useful in the presently disclosed methods for inserting a nucleotide sequence of interest into a host genome in a site-specific manner.

As used herein, the term "construct" can be used in reference to nucleic acid molecules that transfer DNA segment(s), RNA segment(s), or combinations thereof from one cell to another. The term "vector" can be used interchangeably with "construct". The term "construct" can include circular nucleic acid constructs including, but not limited to, plasmid constructs, phagemid constructs, cosmid vectors, as well as linear nucleic acid constructs including, but not limited to, PCR products.

The term "gene therapy" as used herein refers to a general method for treating a pathologic condition in a subject by inserting an exogenous nucleic acid into an appropriate cell(s) within the subject. The nucleic acid is inserted into the cell in such a way as to maintain its functionality, e.g., maintain the ability to express a particular polypeptide. In certain cases, insertion of the exogenous nucleic acid results in the expression of a therapeutically effective amount of a particular polypeptide.

The term "heterologous" when used with reference to a nucleic acid indicates that the nucleic acid comprises one or more subsequences that are not found in the same relationship to each other in nature. For instance, the nucleic acid can be recombinantly produced, having two or more sequences from unrelated genes arranged to make a new functional nucleic acid. For example, in some embodiments, the nucleic acid has a promoter from one gene arranged to direct the expression of a coding sequence from a different gene. Thus, with reference to the coding sequence, the promoter is heterologous. The term "heterologous" can also be used to refer to a nucleic acid that is not native to a host cell. In some embodiments herein, the term "heterologous nucleotide sequence" is used interchangeably with "nucleotide sequence of interest".

"Isolated", as used herein, means that a naturally occurring nucleic acid sequence, DNA fragment, DNA molecule, coding sequence, or oligonucleotide is removed from its natural environment, or is a synthetic molecule or cloned product.

An "LTR" is a long terminal repeat. LTRs are sequences found in retroviruses. The LTR sequence is typically at least several hundred bases long, usually bearing inverted repeats at its termini (often starting with TGAA and ending with TTCA), and flanked with short direct repeats duplicated within the cell DNA sequences flanking an insertion site. The short inverted repeats are involved in integrating the full length viral, retrotransposon, or vector DNA into the host genome. The integration sequence is sometimes called att, for attachment. Inside the LTRs reside three distinct subregions: U3 (the enhancer and promoter region, transcribed from the 5'-LTR), R (repeated at both ends of the RNA), and U5 (transcribed from the 5'-LTR). The LTR and its associated flanking sequences (primer binding sites, splice sites, dimerization linkage and encapsidation sequences) comprise the cis-acting sequences of a retroviral vector. Sources of LTR nucleic acid sequences, e.g., nucleic acid fragments or segments, include, but are not limited to murine retroviruses, murine VL30 sequences, retrotransposons, simian retroviruses, avian retroviruses, feline retroviruses, lentiviruses, avian retroviruses and bovine retroviruses, foamy viruses.

As used herein, the term "non-functional" refers to an element (e.g., a PPT) that does not function as it normally does in vivo. As a non-limiting example, the phrase "non-functional PPT" can refer to a PPT that is absent, mutated, or otherwise modified in such a way that it cannot perform the functions normally performed by the PPT in a retrovirus or a vector based on a retrovirus. Alternatively or in addition, a "non-functional PPT" can refer to a PPT that is present in a vector in a location that prevents the PPT from performing its normal in vivo and/or in vitro functions. Thus, in some embodiments a non-functional PPT is made non-functional by deletion or other mutation of its nucleotide sequence, and in some embodiments a non-functional PPT is made non-functional by being present in a location within a nucleic acid that prevents one or more of its natural biological activities.

The terms "non-integrating" and "integration-deficient" are used interchangeably herein to describe the viral vectors and viral particles of the presently disclosed subject matter. The non-integrating and integration-deficient viral vectors/particles of the presently disclosed subject matter lack a functional PPT such that transduction of these vectors/particles results in production of essentially only 1-LTR episomes. As a result of the dramatic reduction in the production of linear double stranded DNA, the typical capacity to insert nucleic acid sequences into a host's genome through the linear double stranded DNA form is essentially eliminated.

The term "nucleic acid" refers to a deoxyribonucleotide or ribonucleotide polymer in either single- or double-stranded form, and unless otherwise limited, encompasses known analogues of natural nucleotides that hybridize to nucleic acids in manner similar to naturally occurring nucleotides. The terms "nucleic acid", "nucleotide sequence", and "polynucleotide sequence" are herein used interchangeably.

The term "operable combination" refers to a functional arrangement of two or more different nucleic acid sequences wherein their physical proximity to each other results in one or more of the different nucleic acid sequences influencing an activity and/or a behavior of another of the different nucleic acid sequences. In some embodiments, a nucleotide sequence of interest is in operable combination with one or more site-directed recombination sequences. In such embodiments, the nucleotide sequence of interest can be integrated into a desired location in a nucleic acid by operation of a nuclease or recombinase on the one or more site-directed recombination sequences.

The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

A "packaging cassette" encodes components necessary for production of viral particles by a cell transduced by the packaging vector. The packaging cassette optionally includes all of the components necessary for production of viral particles, or optionally includes a subset of the components necessary for viral packaging. For instance, in some embodiments, a packaging cell is transformed with more than one packaging cassette, each of which has a complementary role in the production of a viral particle.

As used herein, the term "polynucleotide" refers to all forms of DNA and RNA, whether single-stranded, double-stranded, or higher order. A polynucleotide can be chemically synthesized or can be isolated from a host cell or organism. A particular polynucleotide can contain both naturally occurring residues as well as synthetic residues.

As used herein, the term "polypurine tract" refers to a sequence of about 15 nucleotides that is present in a retroviral RNA (or in an RNA derived from a retroviral based vector) that can serve as a primer binding site for plus-strand DNA synthesis. See e.g., Rausch & Le Grice (2004) *Int J Biochem Cell Biol* 36:1752-1766.

A "retrovirus" is a single stranded, diploid RNA virus that replicates via reverse transcriptase and a retroviral virion. A retrovirus can be replication-competent or replication incompetent. Representative retroviruses include but not limited to Moloney murine leukemia virus (MoMuLV), Harvey murine sarcoma virus (HaMuSV), murine mammary tumor virus (MuMTV), gibbon ape leukemia virus (GaLV), feline leukemia virus (FLV), Rous Sarcoma Virus (RSV), HTLV-1 and HTLV-2, Mason-Pfizer-monkey virus, bovine leukemia virus, chimpanzee foamy retrovirus, human immunodeficiency viruses HIV-1 and HIV-2, simian immunodeficiency virus (SIV), feline immunodeficiency virus (FIV) and Equine Infectious Anemia virus (EIAV) and foamy viruses.

As used herein, the terms "self inactivating" and grammatical variants thereof refer to vectors and viruses encoded thereby that when they enter a cell produce a cellular form having LTR(s) that are transcriptionally inactive in the infected cell. Generally, this is accomplished by introducing deletions or other debilitating mutations into the LTRs of the vector. As such, a "self inactivating deletion" is a deletion in a viral vector (e.g., a retroviral vector) that after reverse transcription lacks promoter function in the viral LTR(s). It is noted, however, that in some embodiments the self inactivating vector comprises a promoter within the body of the vector (e.g., outside the single LTR or between the two LTRs) that can remain competent to direct transcription of an operably linked nucleotide sequence.

Several terms herein can be used interchangeably. Thus, "virion", "virus", "viral particle", "viral vector", "viral construct", "vector particle", "viral vector transfer cassette" and "shuttle vector" can refer to virus and virus-like particles that are capable of introducing nucleic acids into a cell through a viral-like entry mechanism. Such vector particles can, under certain circumstances, mediate the transfer of genes into the cells they infect. Such cells are designated herein as "target cells". Retroviral vectors have been used to transfer genes by exploiting the viral infectious process. Foreign genes cloned into the retroviral genome can be delivered to cells susceptible to infection or transduction by the retrovirus.

II. Representative Embodiments

Figure 2:
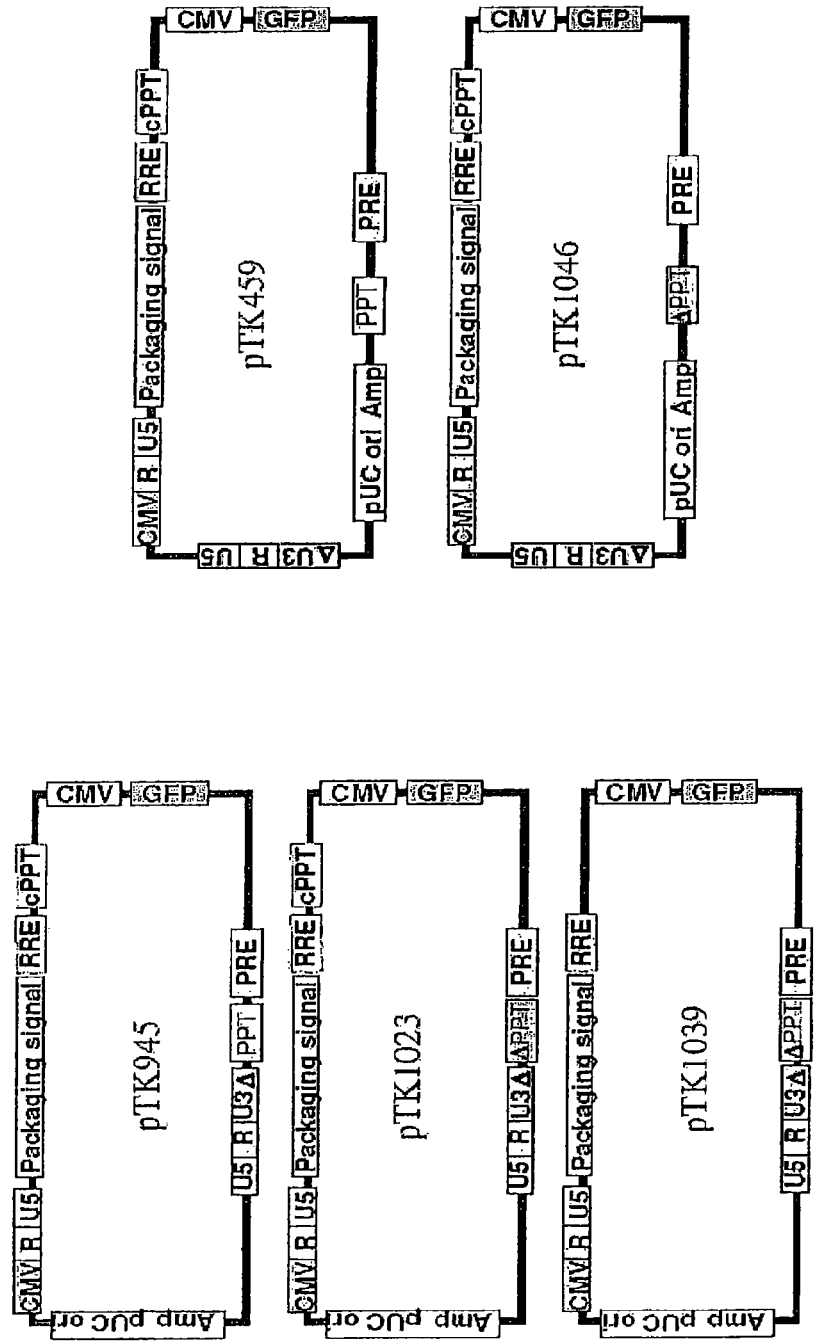
FIG. 2 is a schematic diagram showing representative retroviral vector transfer cassettes of the presently disclosed subject matter. Additional Abbreviations: Amp—ampicillin resistance coding sequence; pUC ori—origin of replication from the pUC series of vectors (Vieira & Messing (1982) *Gene* 19(3):259-268); CMV—major immediate early cytomegalovirus promoter; RRE—Rev Responsive Element of human immunodeficiency virus (HIV); cPPT—central polypurine tract; GFP—green fluorescence protein coding sequence; PRE—Post-transcriptional Regulatory Element; ΔPPT—PPT deletion; U3Δ—LTR U3 Region containing a deletion that renders it self inactivating (SIN); R—LTR R Region; U5—LTR U5 Region.
Figure 3:
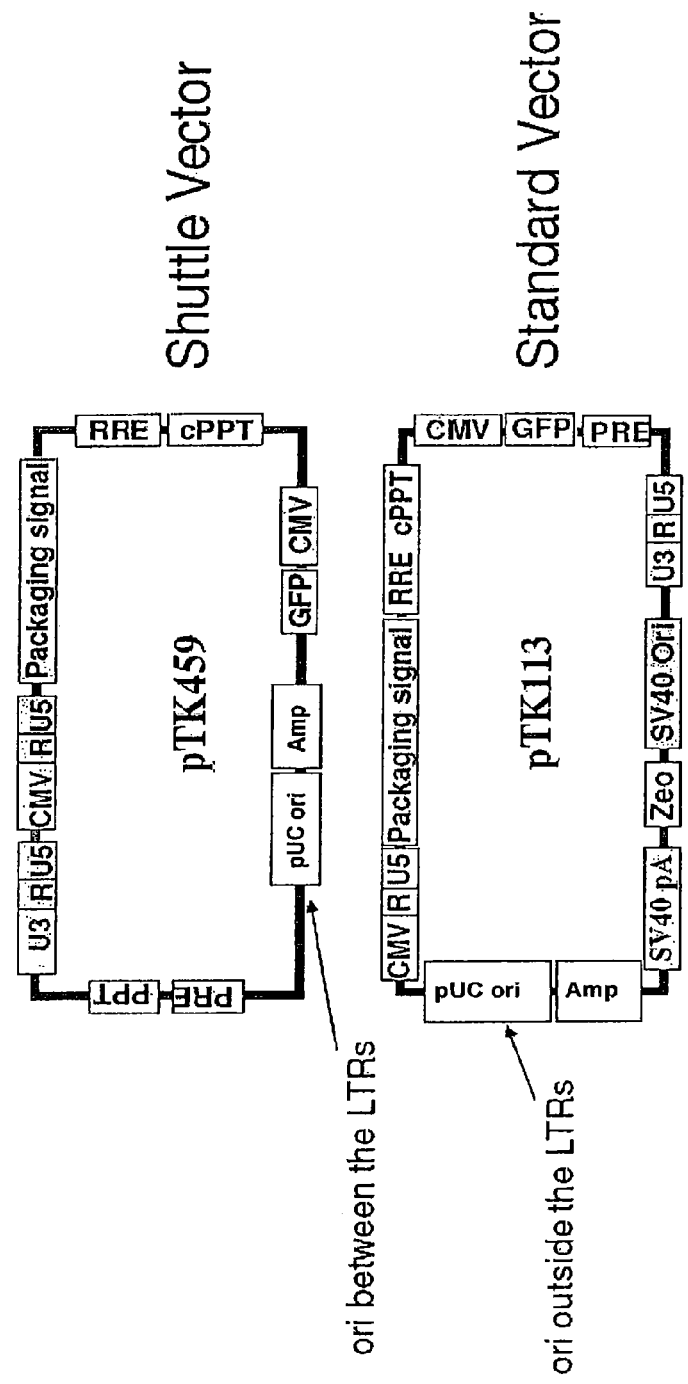
FIG. 3 is a schematic diagram showing a side-by-side comparison of a retroviral vector transfer cassette of the presently disclosed subject matter (e.g., shuttle vector pTK459) and a standard vector (e.g., pTK113).

The presently described subject matter describes integration-defective retroviral vector transfer cassettes from which the parental retroviral polypurine tract (PPT) has been deleted or that otherwise lack a functional PPT (representative embodiments are shown in FIGS. 2 and 3; see also Ma & Kafri (2004) *Mol Ther* 10(1):139-149; Bayer et al. (2008) *Mol Ther* 16(12):1968-1976). Accordingly, in some embodiments of the presently disclosed subject matter, methods and compositions are provided that comprise integration-defective retroviral vectors including, but not limited to, those shown in FIGS. 2 and 3. The presently disclosed subject matter also includes integration-defective retroviral vectors like those represented in FIGS. 2 and 3, but further comprising a viral origin of replication or a sequence that can directly or indirectly mediate replication of the vector nucleic acid by a host. In some embodiments, the viral origin of replication includes but is not limited to EBV-OriP and an SV40 origin of replication. In some embodiments, the viral origin of replication is located upstream of the CMV promoter. In the retroviral vector compositions described herein, production of the vector linear DNA during reverse transcription is dramatically reduced. In fact, the retroviral vector DNA generated in the course of vector-transduction from the presently described vectors is essentially uniformly episomal double-stranded DNA circles containing only 1-LTR (see FIGS. 4-6).

Figure 6:
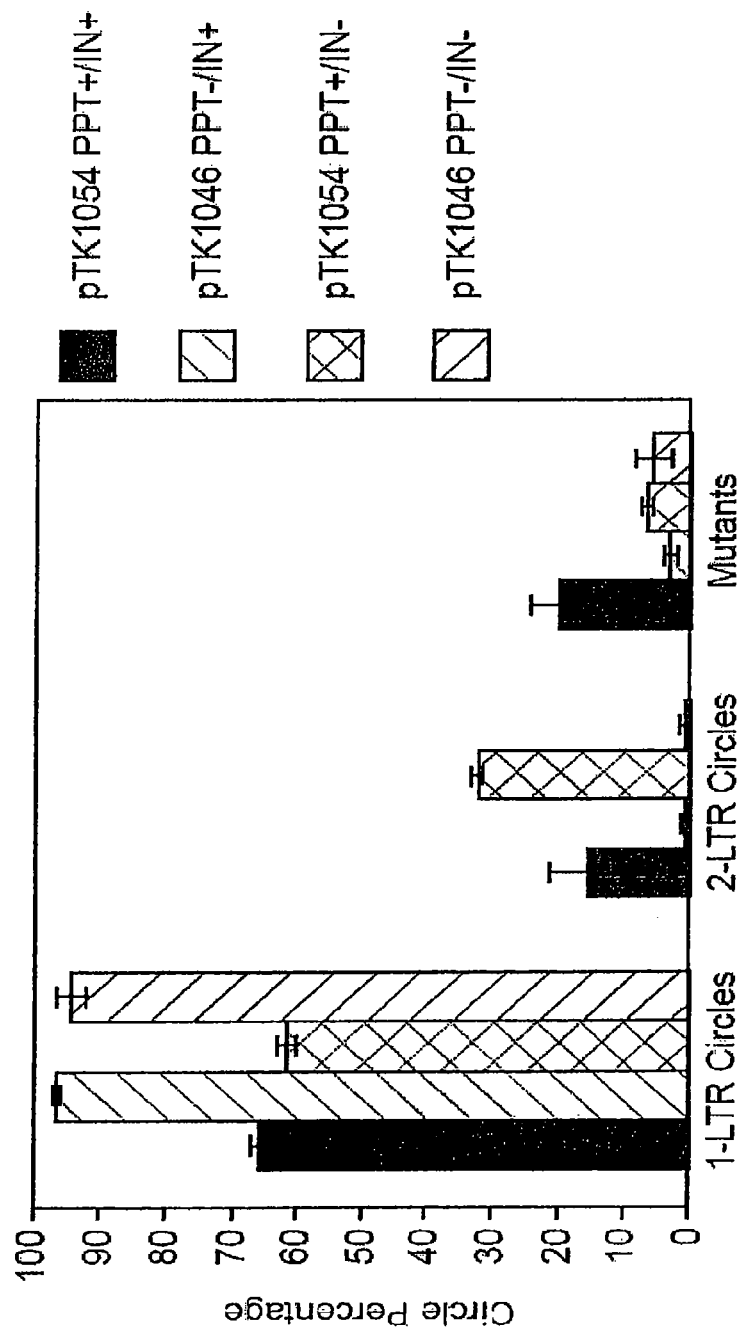
FIG. 6 is a bar graph showing the results of a shuttle-vector assay employed to analyze the relative abundances of 1-LTR, 2-LTR, and mutant circular episomes. 293T cells were transduced with integrating or non-integrating shuttle vectors with (pTK1054; see FIG. 7) or without (TK1046; see FIG. 7) the PPT sequence, and episomes were harvested 16 hours post-transduction. Each transduction was performed in triplicate. Deletion of the PPT led to a decrease in 2-LTR and mutant circular episomes, with a concomitant increase of 1-LTR circular episomes approaching 100%.
Figure 7:
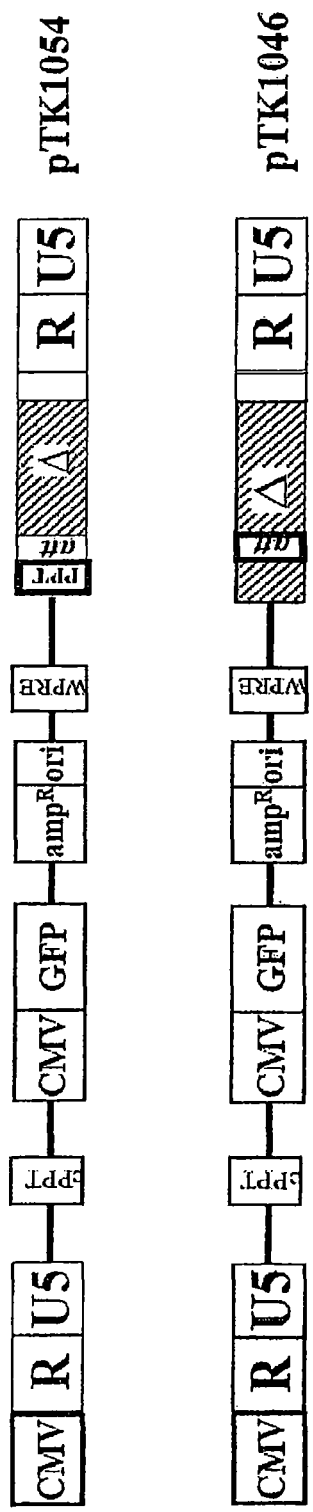
FIG. 7 is a schematic diagram of shuttle vector pTK1054 and shuttle vector pTK1046. As can be seen in the Figure, shuttle vector (pTK1054) includes a PPT sequence, whereas shuttle vector (pTK1046) lacks this sequence. Additional abbreviation: WPRE—Woodchuck hepatitis virus post-transcriptional regulatory element.

For example, a shuttle-vector assay was employed to analyze the relative abundances of 1-LTR, 2-LTR, and mutant circular episomes. 293T cells were transduced with integrating (IN+) or non-integrating (IN−) shuttle vectors with (pTK1054; see FIG. 7) or without (TK1046; see FIG. 7) the PPT sequence, and episomes were harvested 16 hours post-transduction. Each transduction was performed in triplicate. As shown in FIG. 6, deletion of the PPT led to a decrease in 2-LTR and mutant circular episomes, with a concomitant increase of 1-LTR circular episomes approaching 100%. FIG. 7 is a schematic diagram of shuttle vector pTK1054, which includes a PPT sequence, and shuttle vector pTK1046, which lacks the PPT sequence.

Figure 4:
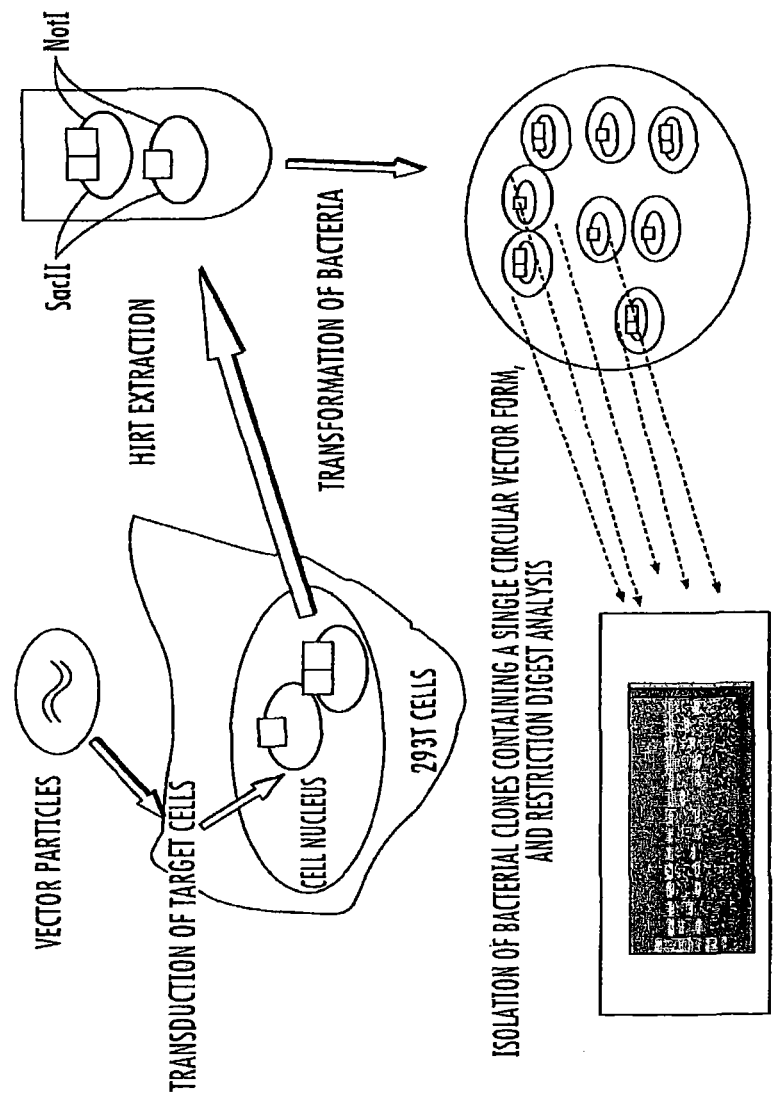
FIG. 4 is a schematic diagram depicting analysis of the ratio of the different HIV-1 episomal forms using a shuttle vector based Hirt assay. Target cells (e.g., 293T cells) were transduced with vector particles using standard techniques, and Hirt extraction (Hirt (1967) *J Mol Biol* 26:365-369) was used to isolate circular forms of double stranded, vector-derived DNA. These circular forms were transformed into bacteria using standard techniques, and bacterial clones containing the circular vector forms were identified. DNA was prepared from the identified bacterial clones, digested with one or more restriction enzymes that cut the circular vector forms once each, and the digested linear DNAs were separated on agarose gels. The presence of one LTR vs. two LTRs can be determined by determining the sizes of the linear molecules.
Figure 5:
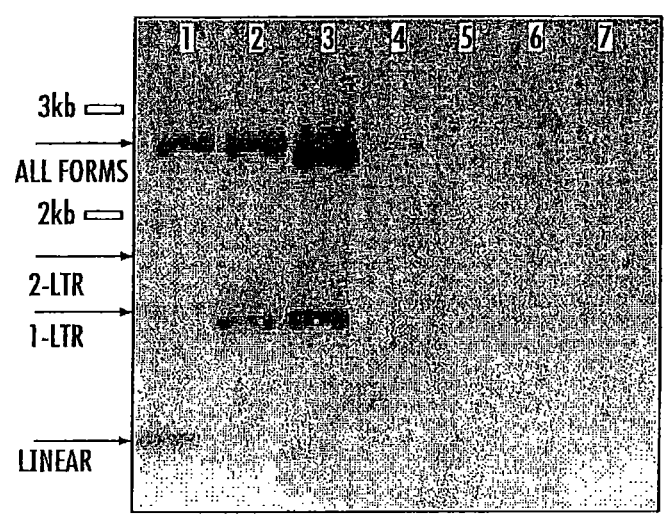
FIG. 5 is an autoradiograph of a gel depicting a Southern blot analysis demonstrating the formation of 1-LTR HIV-1 episomes by PPT- and PPT/cPPT-deleted vectors. 293T cells were transduced with either a traditional HIV-1 vector vTK945 (lanes 1, 4), PPT-deleted vector vTK1023 (lanes 2, 5), or PPT and cPPT-deleted vector, vTK1039 (lanes 3, 6). DNA extracted from the transduced cells at either 16 hours (lanes 1-3), or 5 passages (lanes 4-6) post-transduction was subjected to Southern blot analysis. The majority of the episomal vector DNA generated by the WT vector, vTK945 was linear (lane 1). Furthermore, only integrated vTK945 genomes could be detected following 5 cell passages in culture (lane 4). In contrast, only 1-LTR forms of vTK1023 and vTK1039 could be detected at 24 hours post-transduction. The fact that the genome of these vectors could not be detected after 5 passages post-transduction (lanes 5, 6) indicates that the PPT-deleted vectors are integration defective (as expected from the lack of linear vector forms).

One possible mechanism of 1-LTR episomal HIV-1 vector formation according to the methods and compositions of the presently disclosed subject matter was characterized and representative data are shown in FIGS. 4 & 5. Based on the fact that the level of 1-LTR vector forms was not reduced in cell lines defective in homologous recombination, the role of reverse transcription in the formation of 1-LTR vector forms was a focus. Specifically, it was demonstrated that deletion of the vector's polypurine tract (PPT) dramatically reduced the formation of linear dsDNA vector forms and consequently rendered the vector integration-defective (FIG. 5). As shown in FIG. 5, only 1-LTR vector forms could be detected in 293T cells transduced with PPT deleted vector. While it is not desired to be held to any particular theory of operation, it is believed that the deletion of the PPT can allow plus-strand DNA synthesis from a cryptic RNA primer located upstream of the cPPT. This can prevent the "second-jump", resulting in the formation of 1-LTR vector forms only. Alternatively or in addition, second strand synthesis can be initiated from the primer binding site (PBS) and/or a cryptic site.

In some embodiments of the presently disclosed subject matter, compositions are provided comprising integration-defective retroviral vector transfer cassettes lacking a functional polypurine tract (PPT). In some embodiments, isolated nucleic acids are provided comprising a heterologous nucleotide sequence, one or two retroviral long terminal repeats (LTRs), a packaging signal, a rev responsive element, and a eukaryotic promoter, wherein the nucleic acid lacks a functional PPT. In some embodiments, the isolated nucleic acid further comprises a bacterial origin of replication situated between the two LTRs. In some embodiments, the isolated nucleic acid further comprises a bacterial selection marker (i.e., a bacterial coding sequence the expression of which permits a cell to grow in the presence of a compound that would otherwise prevent its growth and/or kill it). In some embodiments, the isolated nucleic acid further comprises a viral origin of replication or a sequence that can directly or indirectly mediate replication of the vector nucleic acid by a host. In some embodiments, the viral origin of replication includes but is not limited to Epstein Barr Virus (EBV) OriP and an SV40 origin of replication. In some embodiments, vectors are provided comprising the nucleic acids. In some embodiments, recombinant retroviral particles are provided comprising the vectors.

In some embodiments, inducible retroviral vector packaging cell lines are provided comprising the vectors and at least one construct coding for proteins required for the retroviral vector to be packaged.

In some embodiments, methods are provided for producing integration-defective vector particles, comprising transfecting a packaging cell line with an integration-defective retroviral vector transfer cassette lacking a functional PPT, wherein the packaging cell line provides proteins for the retroviral vector to be packaged.

In some embodiments, retroviral vector kits are provided comprising an integration-defective retroviral vector transfer cassette lacking a functional PPT; and a packaging cell line comprising at least one construct coding for proteins required for the retroviral vector to be packaged.

In some embodiments, methods are provided for achieving gene expression of a nucleotide sequence of interest in the cells of an animal substantially without integration of the nucleotide sequence into the animal genome, comprising infecting the cells with an integration-defective retroviral particle of the presently disclosed subject matter that comprises the nucleotide sequence of interest. In some embodiments, the integration-defective retroviral vector transfer cassettes of the presently disclosed subject matter that comprise either a viral origin of replication or a sequence that can mediate replication of the vector nucleic acid by the host cells can be maintained in dividing target cells. Conversely, in applications where only transient gene expression is desired, the integration-defective retroviral vector transfer cassettes of the presently disclosed subject matter that do not comprise an origin of replication are useful as they are not maintained in dividing cells. For example, in some embodiments, the integration-defective retroviral vector transfer cassettes of the presently disclosed subject matter lacking an origin of replication are useful for obtaining transient expression of a gene of interest in stem cells. In some embodiments, the gene of interest is a gene that directs differentiation of the stem cells. In some embodiment, the stem cells are useful for gene therapy.

In some embodiments, the sequence that can directly or indirectly mediate replication of the vector nucleic acid by the host cell includes but is not limited to a sequence recognized by the host-cell replication machinery; a sequence encoding a protein that can associate with and/or modulate host-cell replication machinery; and a sequence encoding a protein that can associate with the protein that can associate with and/or modulate host-cell replication machinery.

Accordingly, the non-integrating retroviral vector compositions and methods of the presently disclosed subject matter can be used to avoid insertional mutagenesis. In some embodiments, methods are provided for achieving gene expression of a nucleotide sequence of interest in the cells of an animal by targeting integration of the nucleotide sequence into the animal genome. In some embodiments, the integration-defective vector compositions of the presently disclosed subject matter are useful as they are significantly more efficient than currently used non-integrating retroviral systems in the context of applications based on circular vector forms, including but not limited to FLP and Cre mediated vector integration. For example, the non-integrating retroviral vector compositions and methods of the presently disclosed subject matter can be used to obtain targeted integration of a gene of interest into the genome of a host by combining the non-integrating retroviral vector compositions and methods of the presently disclosed subject matter with known autonomous replication systems and site directed recombination systems. In some embodiments, the integration-defective retroviral vector transfer cassettes of the presently disclosed subject matter are useful for obtaining expression of a gene of interest in stem cells. In some embodiments, the stem cells are useful for gene therapy.

In some embodiments of the presently disclosed subject matter, integration-defective retroviral vector transfer cassettes lacking a functional polypurine tract (PPT) are provided that comprise a heterologous sequence. In some embodiments, the heterologous sequence includes but is not limited to one or more marker genes, therapeutic genes, antiviral genes, antitumor genes, cytokine genes, genes encoding antigens, sequences that can associate with the host chromatin, sequences that encode a protein that can associate with the host DNA and the host chromatin and the nucleic acid of the vector, sequences that encode a protein having DNA methylation activity, DNA demethylation activity, cytosine deaminase activity, and combinations thereof. In some embodiments, a sequence that can associate with the host chromatin is selected from the group consisting of a matrix-associated region (MAR) and a scaffold/matrix-attachment region (S/MAR). In some embodiments, the marker genes include but are not limited to β-galactosidase gene, hygromycin gene, blastocidin gene, MGMT gene, neomycin gene, puromycin gene, cytosine deaminase gene, secreted alkaline phosphatase gene, fluorescent protein genes, and combinations thereof.

In some embodiments, vectors are provided comprising the nucleic acids of the presently disclosed subject matter. In some embodiments, the vectors comprise only a single LTR. In some embodiments, the vector comprises sequences from at least two different retroviruses. In some embodiments, the at least two different retroviruses includes a lentivirus. In some embodiments, the vector LTR comprises sequences from at least two different retroviruses. In some embodiments, the at least two different retroviruses includes a lentivirus. In some embodiments, the vector comprises sequences from at least two different retroviruses and at least one of the sequences encodes a cis element that provides for cross-packaging of the vector in a viral particle. In some embodiments, the cis element includes but is not limited to a RRE, an Env gene fragment from the region flanking the RRE and a cPPT. In some embodiments, the integration-defective retroviral vector transfer cassettes lacking a functional PPT include retroviral vector transfer cassettes comprising sequences from at least two different retroviruses and contain a PPT, but the PPT is effectively rendered non-functional.

In some embodiments, the presently disclosed subject matter provides methods for inserting a nucleotide sequence of interest into a host genome in a site-specific manner, comprising transducing a compatible host cell with the integration-defective vectors disclosed herein, comprising in operable combination the nucleotide sequence of interest and one or more site-directed recombination sequences; and transfecting or transducing the compatible host cell with a nucleic acid comprising a sequence encoding a nuclease or recombinase that can mediate site-specific integration at the recombination sequence.

In some embodiments, there is no second transfection/transduction step and the transfection/transduction occurs all in the same step. In some embodiments, the recombinase capable of mediating site-specific integration at the recombination sequence is Cre or FLP. In some embodiments, there is no second transfection/transduction step and the nucleic acid comprising a sequence encoding a nuclease or recombinase is the integration-defective vector. In some embodiments, the transfection/transduction step occurs all in the same step and the nucleic acid comprising a sequence encoding a nuclease or recombinase is on a separate vector or plasmid or nucleic acid molecule than the integration-defective vector. In some embodiments, the sequence recognized by the nuclease or recombinase that can mediate site-specific integration is a loxP site or a pseudo-loxP site. In some embodiments, the sequences are recognition sites for Cre or Cre variants. In some embodiments, the gene to be inserted can be located in the U3 region of the 3' LTR sequence. In some embodiments, the vector includes one or more reporter genes.

In some embodiments, the presently disclosed subject matter provides methods for inserting a nucleotide sequence of interest into a host cell genome in a non-specific manner, comprising: transducing a host cell with an integration-defective vector of the presently disclosed subject matter comprising in operable combination the nucleotide sequence of interest and one or more transposon sequences; and transfecting or transducing the compatible host cell with a nucleic acid comprising a sequence encoding a transposase that can mediate integration into the host genome. In some embodiments, there is no second transfection/transduction step and the transfection/transduction occurs all in the same step. In some embodiments, the transfection/transduction step occurs all in the same step and the nucleic acid comprising a sequence encoding a transposase is the integration-defective vector. In some embodiments, the transfection/transduction step occurs all in the same step and the nucleic acid comprising a sequence encoding a transposase is on a separate vector or plasmid or nucleic acid molecule than the integration-defective vector. In some embodiments, the transposon and transposase are a mariner-type such as Sleeping Beauty (see e.g. U.S. Pat. No. 6,613,752; Robertson (1993) *Nature* 362:241-245; Ivics et al. (1997) *Cell* 91:501-510; Plasterk et al. (1999) *Trends Genet* 15:326-332; Zayed et al. (2003) *Nuc. Acid Res* 31(9):2313-2322; Arkhipova et al. (2005) *Proc Natl Acad Sci USA* 102:11781-11786).

The presently described subject matter describes the development of non-integrating retroviral vector compositions and methods. The retroviral vector genomes generated by the compositions and methods of the presently described subject matter in the course of vector-transduction are substantially uniformly, episomal double-stranded 1-LTR DNA circular forms. The fact that essentially only 1-LTR forms are generated allows for better control of the non-integrating vectors. Accordingly, the non-integrating retroviral vector compositions and methods of the presently disclosed subject matter have numerous uses and benefits for achieving gene expression of nucleotide sequences of interest in animal cells, including a decreased risk of induction of the DNA damage repair response and a significant increase in efficiency when used in combination with applications based on circular vector forms including but not limited to FLP and Cre mediated vector integration.

It will be understood that various details of the presently disclosed subject matter may be changed without departing from the scope of the presently disclosed subject matter. Furthermore, the foregoing description is for the purpose of illustration only, and not for the purpose of limitation.

What is claimed is:

1. A retroviral vector kit comprising:
   (a) an integration-defective retroviral RNA vector transfer cassette comprising:
      (i) a 5' long terminal repeat (5' LTR) and a 3' long terminal repeat (3' LTR);
      (ii) a packaging signal;
      (iii) a primer binding site (PBS);
      (iv) a promoter, optionally a eukaryotic promoter; and
      (v) a mutation, a deletion, or other modification of the 3' polypurine tract (3' PPT),
      wherein the 3' PPT is absent or otherwise non-functional, wherein the retroviral RNA vector transfer cassette is integration defective, and wherein the integration-defective retroviral RNA vector transfer cassette can be reverse-transcribed; and
   (b) a packaging cell line comprising at least one construct encoding one or more proteins required for the retroviral RNA vector transfer cassette to be packaged.

2. The retroviral vector kit of claim 1, wherein the retroviral RNA transfer cassette further comprises a nucleotide sequence of interest (NOI).

3. The retroviral vector kit of claim 2, wherein the NOI is selected from the group consisting of one or more marker genes, therapeutic genes, antiviral genes, antitumor genes, cytokine genes, genes encoding antigens, sequences that can associate with the host chromatin, sequences that encode a protein that can associate with the host DNA and the host chromatin and the nucleic acid of the vector, sequences that encode a protein having DNA methylation activity and combination thereof.

4. The retroviral vector kit of claim 3, wherein the one or more marker genes are selected from the group consisting of β-galactosidase gene, hygromycin gene, blastocidin gene, MGMT gene, neomycin gene, puromycin gene, cytosine deaminase gene, secreted alkaline phosphatase gene, fluorescent protein genes, and combinations thereof.

5. The retroviral vector kit of claim 1, wherein the retroviral RNA transfer cassette further comprises a post-transcriptional regulatory element.

6. A method of producing integration-defective vector particles, comprising introducing into a packaging cell line an integration-defective retroviral RNA vector transfer cassette comprising:
   (i) a 5' long terminal repeat (5' LTR) and a 3' long terminal repeat (3' LTR);
   (ii) a packaging signal;
   (iii) a primer binding site (PBS);
   (iv) a promoter, optionally a eukaryotic promoter; and
   (v) a mutation, a deletion, or other modification of the 3' polypurine tract (3' PPT),
   wherein the 3' PPT is absent or otherwise non-functional, wherein the retroviral RNA vector transfer cassette is integration defective, and wherein the integration-defective retroviral RNA vector transfer cassette can be reverse-transcribed, wherein the packaging cell line provides proteins for the retroviral RNA vector transfer cassette to be packaged.

7. The method of claim 6, wherein the retroviral RNA transfer cassette further comprises a nucleotide sequence of interest (NOI).

8. The method of claim 7, wherein the NOI is selected from the group consisting of one or more marker genes, therapeutic genes, antiviral genes, antitumor genes, cytokine genes, genes encoding antigens, sequences that can associate with the host chromatin, sequences that encode a protein that can associate with the host DNA and the host chromatin and the nucleic acid of the vector, sequences that encode a protein having DNA methylation activity and combination thereof.

9. The method of claim 8, wherein the one or more marker genes are selected from the group consisting of β-galactosidase gene, hygromycin gene, blastocidin gene, MGMT gene, neomycin gene, puromycin gene, cytosine deaminase gene, secreted alkaline phosphatase gene, fluorescent protein genes, and combinations thereof.

10. The method of claim 6, wherein the retroviral RNA transfer cassette further comprises a post-transcriptional regulatory element.

* * * * *

UNITED STATES PATENT AND TRADEMARK OFFICE
CERTIFICATE OF CORRECTION

PATENT NO.         : 10,017,785 B2                                              Page 1 of 1
APPLICATION NO.    : 15/790530
DATED              : July 10, 2018
INVENTOR(S)        : Tal Kafri It is certified that error appears in the above-identified patent and that said Letters Patent is hereby corrected as shown below:

In the Specification

Column 2, Line 7: Please correct "SW" to read -- SIV --

Signed and Sealed this
Ninth Day of October, 2018

Andrei Iancu
*Director of the United States Patent and Trademark Office*